US007247307B2

(12) United States Patent
Szu et al.

(10) Patent No.: US 7,247,307 B2
(45) Date of Patent: Jul. 24, 2007

(54) **VACCINES AGAINST *ESCHERICHIA COLI* O157 INFECTION**

(75) Inventors: Shousun Chen Szu, Bethesda, MD (US); John B. Robbins, Chevy Chase, MD (US); Edward Konadu, deceased, late of Ashanti Region (GH); Yvonne Ageyman Konadu, legal representative, Bronx, NY (US)

(73) Assignee: The United States of America as represented by the Secretary of the Department of Health and Human Services, Washington, DC (US)

( * ) Notice: Subject to any disclaimer, the term of this patent is extended or adjusted under 35 U.S.C. 154(b) by 251 days.

(21) Appl. No.: 11/015,436

(22) Filed: Dec. 16, 2004

(65) Prior Publication Data

US 2005/0158339 A1     Jul. 21, 2005

Related U.S. Application Data

(62) Division of application No. 09/744,289, filed as application No. PCT/US98/14976 on Jul. 20, 1998, now Pat. No. 6,858,211.

(51) Int. Cl.
*A61K 39/108* (2006.01)
*A61K 39/385* (2006.01)

(52) U.S. Cl. .............................. 424/241.1; 424/234.1; 424/203.1; 424/197.11; 424/193.1

(58) Field of Classification Search .................... None
See application file for complete search history.

(56) References Cited

U.S. PATENT DOCUMENTS

| | | | |
|---|---|---|---|
| 4,141,970 A | 2/1979 | Childlow et al. | |
| 4,356,170 A | 10/1982 | Jennings et al. | |
| 4,711,779 A | 12/1987 | Porro et al. | |
| 5,153,312 A | 10/1992 | Porro | |
| 5,204,097 A | 4/1993 | Arnon et al. | |
| 5,306,492 A | 4/1994 | Porro | |
| 5,354,661 A | 10/1994 | Doyle et al. | |
| 5,370,872 A | 12/1994 | Cryz et al. | |
| 5,371,197 A | 12/1994 | Marburg et al. | |
| 5,512,282 A | 4/1996 | Krivan et al. | |
| 5,552,144 A | 9/1996 | Samuel et al. | |
| 5,585,100 A | 12/1996 | Mond et al. | |
| 5,693,326 A | 12/1997 | Lees | |
| 5,747,272 A | 5/1998 | O'Brien et al. | |
| 5,773,007 A | 6/1998 | Penny et al. | |
| 5,785,973 A | 7/1998 | Bixler et al. | |
| 5,955,293 A | 9/1999 | Keusch et al. | |
| 6,162,441 A | 12/2000 | Chae et al. | |
| 6,310,043 B1 | 10/2001 | Bundle et al. | |
| 6,410,024 B1 | 6/2002 | Burnie et al. | |
| 6,607,725 B2 * | 8/2003 | Gu et al. | 424/184.1 |
| 6,632,437 B1 * | 10/2003 | Schneerson et al. | 424/193.1 |
| 6,797,275 B1 * | 9/2004 | Kossaczka et al. | 424/258.1 |

OTHER PUBLICATIONS

Konadu et al 1994 (reference of record).*
Konadu et al (symposium, Jun. 22-26, 1997, reference of record).*
Konadu et al (Feb. 1998, reference of record).*
96th General Meeting of the American Society for Microbiology, New Orleans, Louisiana, USA May 19-23, 1996; Abstracts of the General Meeting of the American Society for Microbiology, vol. 96(0), pp. 276, 1996; Evaluation of *Escherichia coli* O157 O-specific polysaccharide *Pseudomonas aeruginosa* recombinant exoprotein A (rEPA) conjugates(abstract).*
Chart et al., "Antibody Cross-Reactions with Lipopolysaccharide from *E coli* O157 After Cholera Vaccination," *Lancet* 341:1282 (1993).
Cohen et al., "Safety and Immunogenicity of Investigational *Shigella* Conjugate Vaccines in Israeli Volunteers," *Infect. Immun.* 64:4074-4077 (1996).
Cohen et al., "Double-Blind Vaccine-Controlled Randomised Efficacy Trial of an Investigational *Shigella sonnei* Conjugate Vaccine in Young Adults," *Lancet* 349:155-159 (1997).
Fattom et al., "Serum Antibody Response in Adult Volunteers Elicited by Injection of *Streptococcus pneumoniae* Type 12F Polysaccharide Alone or Conjugated to Diphtheria Toxoid," *Infect. Immun.* 58:2309-2312 (1990).
Greatorex et al., "Humoral Immune Responses to Shiga-Like Toxins and *Escherichia coli* O157 Lipopolysaccharide in Hemolytic-Uremic Syndrome Patients and Healthy Subjects," *J. Clin. Microbiol.* 32:1172-1178 (1994).

(Continued)

*Primary Examiner*—Mark Navarro
*Assistant Examiner*—Ginny Allen Portner
(74) *Attorney, Agent, or Firm*—Klarquist Sparkman, LLP

(57) ABSTRACT

This invention relates to conjugates of the O-specific polysaccharide of *E. coli* O157 with a carrier, and compositions thereof, and to methods of using of these conjugates and/or compositions thereof for eliciting an immunogenic response in mammals, including responses which provide protection against, or reduce the severity of, bacterial infections. More particularly it relates to the use of polysaccharides containing the tetrasaccharide repeat unit: (→3)-α-DGalpNAc-(1→2)-α-D-PerpNAc-(1→3)-α-L-Fucp-(1→4)-β-D-Glcp-(1→), and conjugates thereof, to induce serum antibodies having bactericidal (killing) activity against hemolytic-uremic syndrome (HUS) causing *E. coli*, in particular *E. coli* O157. The conjugates, and compositions thereof, are useful as vaccines to induce serum antibodies which have bactericidal or bacteriostatic activity against *E. coli*, in particular *E. coli* O157, and are useful to prevent and/or treat illnesses caused by *E. coli* O157.

The invention further relates to the antibodies which immunoreact with the O-specific polysaccharide of *E. coli* O157 and/or the carrier, that are induced by these conjugates and/or compositions thereof. The invention also relates to methods and kits using one or more of the polysaccharides, conjugates or antibodies described above.

10 Claims, No Drawings

OTHER PUBLICATIONS

Konadu et al., "Synthesis, Characterization, and Immunological Properties in Mice of Conjugates Composed of Detoxified Lipopolysaccharide of *Salmonella paratyphi* A Bound to Tetanus Toxoid, with Emphasis on the Role of *O* Acetyls," *Infect. Immun.* 64:2709-2715 (1996).

Robbins et al., "Polysaccharidide-Protein Conjugates: A New Generation of Vaccines," *J. Infect. Dis.* 161:821-832 (1990).

Szu et al., "Vi Capsular Polysaccharide-Protein Conjugates for Prevention of Typhoid Fever," *J. Exp. Med* 166:1510-1524 (1987).

Ashkenazi et al., "Anticytotoxin-Neutralizing Antibodies in Immune Globulin Preparations: Potential Use in Hemolytic-Uremic Syndrome," *J. Pediatr.* 113:1008-1014 (1988).

Bitzan et al., "Differences in Verotoxin Neutralizing Activity of Therapeutic Immunoglobulins and Sera from Health Controls," *Infection* 21:140-145 (1993).

Brief Notes: Researchers at the National Institutes of Health, *Food Chemical News*, vol. 39, No. 52, (Abstract), Feb. 16, 1998.

Chart et al., "Serum Antibodies to *Escherichia coli* Serotype O157:H7 in Patients with Hemolytic Uremic Syndrome," *J. Clin. Microbiol.* 27:285-290 (1989).

Chu et al., "Preparation, Characterization, and Immunogenicity of Conjugates Composed of the O-Specific Polysaccharide of *Shigella dysenteriae* Type 1 (Shiga's Bacillus) Bond to Tetanus Toxoid," *Infect. Immun.* 59:4450-4458 (1991).

Claesson et al., "Clinical and Immunologic Responses to the Capsular Polysaccharide of Haemophilus Influenzae Type b Alone or Conjugated to Tetanus Toxoid in 18- to 23- Month Old Children," *J. Pediatr.* 112:695-702 (1988).

Conference Discusses Ways to Reduce *E. coli* at Farm and Slaughter, *Food Chemical News*, vol. 37, No. 9 (Abstract), Apr. 24, 1995.

Conlan et al., "Parenteral Immunization with a Glycoconjugate Vaccine Containing the O157 Antigen of *Escherichia coli* O157:H7 Elicits a Systemic Humoral Immune Response in Mice, but Fails to Prevent Colonization by the Pathogen," *Can. J. Mcirobiol. Rev.* 45:279-286 (1999). Abstract only.

Cryz, Jr. et al., "Syntheis and Characterization of *Escherichia coli* O18 O-Polysaccharide Conjugate Vaccines," *Infect. Immun.* 58:373-377 (1990).

Cryz, Jr. et al., "Safety and Immunogenicity of *Escherichia coli* O18 O-Specific Polysaccharide (O-PS)-Toxin A and O-PS-Cholera Toxin Conjugate Vaccines in Humans," *J. Infect. Dis.* 163:1040-1045 (1991).

Dick and Beurret, "Glycoconjugated of Bacterial Carbohydrate Antigens. A Survey and Consideration of Design and Preparation Factors," *Contrib. Microbiol. Immunol.* 10:48-114 (1989).

*E. coli*, VTEC Research Reviewed at IAMFES Meeting, *Food Chemical News*, vol. 38, No. 21 (Abstract), Jul. 15, 1996.

*E. coli* US Experts: Food Poisoning Vaccine Works, *Vaccine Weekly*, (Abstract), Mar. 2, 1998.

Fattom et al., "Laboratory and Clinical Evaluation of Conjugate Vaccines Composed of *Staphylococcus aureus* Type 5 and and Type 8 Capsular Polysaccharides Bound to *Pseudomonas aerugonosa* Recombinant Exoprotein A," *Infect. Immun.* 61:1023-1032 (1993).

Gupta et al., "Comparative Immunogenicity of Conjugates Composed of *Escherichaio coli* O111 O-Specific Polysaccharide, Prepared by Treatment and Acetic Acid of Hydrazine, Bound to Tetanus Toxoid by Two Synthetic Schemes," *Infect. Immun.* 63:2805-2810 (1995).

Harari et al., "Synthetic Peptides of Shiga Toxin B Subunit Induce Antibodies Which Neutralize Its Biological Activity," *Infect, Immun.* 56:1618-1624 (1988).

Havens et al., "Effects of Human Intravenous Immune Globulin on Diarrhea Caused by Shiga-Like Toxin I and Shiga-Like Toxin II in Infant Rabbits," *Microbiol. Immunol.* 36:1077-1085 (1992).

Human Testing of *E. coli* O157:H7 Vaccine, *Food Chemical News*, vol. 37, No. 19 (Abstract), Jul. 3, 1995.

Islam et al., "Production and Characterization of Monoclonal Antibodies with Therapeutic Potentials Against Shiga Toxin," *J. Clin. lab. Immunol.* 33:11-16 (1990).

Johnson, et al., "Serum Antibody Responses of Cattle Following Experimental Infection with *Escherichia coli* O157:H7," *Infect. Immun.* 64:1879-1883 (1996).

Konadu et al., "Preparation, Characterization, and Immunological Properties in Mice of *Escherichia coli* O157 O-Specific Polysaccharide-Protein Conjugate Vaccines," *Infect. Immun.* 62:5048-5054 (1994).

Konadu et al., "Synthesis and Immunologic Properties of O-Specific Polysaccharide-Protein Conjugate Vaccines for Prevention and Treatment of Infections with *Escherichia coli* O157 and Other Causes of the Hemolytic-Uremic Syndrome," In *Escherichia coli O157:H7 and other Shiga Toxin-Producing E. coli Strains*, Eds. JB. Kaper and A.D. O'Brien, American Society for Microbiology, Washington, pp. 419-424 (Jun. 19, 1998) (based on a symposium and workshop held in Baltimore, MD, Jun. 22-26, 1997).

Konadu et al., "Investigational Vaccine for *Escherichia coli* O157: Phase 1 Study of O157 O-Specific Polysacchide-*Pseudomonas aseruginosa* Recombinant Exoprotein A Conjugates in Adults," *J. Infect. Dis.* 177:383-387 Feb. (1998).

Kondau et al., "Syntheses and Immunologic Properties of *Escherichia coli* O157 O-Specific Polysaccharide and Shiga Toxin 1 B Subunit Conjugates in Mice," *Infect. Immun.* 67:6191-6193 (1999).

Ludwig et al., "*Escherichia coli* O157 Fails to Induce a Long-Lasting Lipopolysaccharide-Specific, Measurable Humoral Immune Response in Children with Hemolytic-Uremic Syndrome," *J. Infect. Dis.* 186:566-569 (2002).

Lovett, R.A., "Training a Molecular Gun on Killer *E. coli,*" *Science* 282:1404 (1998).

Meeting schedule and slides from presentation by Shousun C. Szu entitled "LPs-Based Vaccine" held on Jun. 26, 1997 during a symposium and workshop of the American Society for Microbiology, Washington, DC, held in Baltimore, MD, Jun. 22-26, 1997 (with re-typed text of the slide labeled "Why is Conjugate Better" and computer printout of "Anti-LPS IgS" (Preliminary Slide).

Padhye et al., "Production and Characterization of a Monoclonal Antibody Specific for Enterohemorrhagic *Escherichia coli* of Serotypes O157:H7 and O26:H11," *J. Clin. Microbiol.* 29:99-103 (1991).

Product News: *Escherichia coli* Vaccine Specific to *E. coli* O157 Might be Useful for Prophylaxis and Treatment, *Inpharma*, (Abstract), Feb. 24, 1998.

Qadri, et al., Advances in Musosal Immunology, edited by J. Meskecky et al., 1995, Advances in Experimental Medicine and Biology, 1995, vol. 371/B, pp. 923-926.

Robbins et al., "O-Specific Side-Chain Toxin-Protein Conjugates as Parenteral Vaccines for the Prevention of Shigellosis and Related Diseases," *Rev. Infect. Dis.* 13:S362-S365 (1991).

Robbins et al., "Hypothesis for Vaccine Development: Protective Immunity to Enteric Diseases Caused by Nontyphoidal Salmonellae and Shigellae May be Conferred by Serum IgG Antibodies to the O-Specific Polysaccharide of Their Lipopolysaccharides," *Clin. Infect. Dis.* 15:346-61 (1992).

Robbins et al., "Perspective: Hypotheses: Serum IgG Antibody is Sufficient to Confer Protection Against Infectious Diseases by Inactivating the Inoculum," *J. Infect. Dis.* 171:1387-1398 (1995).

Ryd, Marie, Ph.D., Thesis, 1992, Karolinska Institutet (Sweden) (0658) vol. 55/02-C of Dissertation Abstracts International, p. 432.

Sarnaik et al., "Studies on Pneumococcus Vaccine Alone or Mixed with DTP and on Pneumococcus Type 6B and *Haemophilus influenzae* Type b Capsular Polysaccharide-Tetanus Toxoid Conjugates in Two- to Five-Year Old Children with Sickle Cell Amemia," *Pediatric Infect. Dis. J.* 9:181-186 (1990).

Schmitt et al., "Two Copies of Shiga-Like Toxin II-Related Genes Common in Enterohemorrhagic *Escherichia coli* Strains are Responsible for the Antigenic Heterogeneity of the O157:H⁻Strain E32511," *Infect. Immun.* 59:1065-1073 (1991).

Schneerson et al., "Quantitative and Qualitative Analyses of Serum Antibodies Elicited in Adults by *Haemophilus influenzae* Type b and Pneumococcus Type 6A Capsular Polysaccharide-Tetanus Toxoid Conjugates," *Infect. Immun.* 52:519-528 (1986).

Sjogren et al., "Influence of Shiga-Like Toxin Production in Enteric Infection with an Enteropathogenic *Escherichia coli* Strain," *Gastroenterol.* 92:1643 (1987).

Strockbrine et al., "Characterization of Monoclonal Antibodies against Shiga-Like Toxin from *Escherichia coli*," *Infect. Immun.* 50:695-700 (1985).

Taylor et al., "Synthesis, Characterization, and Clinical Evaluation of Conjugate Vaccines Composed of the O-Specific Polysaccharides of *Shigella dysentariae* Type 1, *Shigella flexneri* Type 2a, and *Shigella sonnei* (*Plesiomonas shigelloides*) Bound to Bacterial Toxoids," *Infect. Immun.* 61:3678-3687 (1993).

Vernozy-Rozand, C., "Detection of *Escherichia coli* O157:H7 and Other Verocytotoxin-Producing *E. coli* (VTEC) in Food," *J. Appl. Microbiol.* 82:537-551 (1997).

Weinstein et al., "In Vivo Formation of Hybrid Toxins Comprising Shiga Toxin and the Shiga-Like Toxins and Role of the B Subunit in Localization and Cytotoxic Activity," *Infect. Immun.* 57:3743-3750 (1989).

You Should Know, *Food Institute Report*, vol. 71, No. 7, (Abstract), Feb. 16, 1998.

* cited by examiner

VACCINES AGAINST *ESCHERICHIA COLI* O157 INFECTION

CROSS REFERENCE TO RELATED APPLICATIONS

This application is a divisional of parent U.S. application Ser. No. 09/744,289, filed Aug. 1, 2001, now U.S. Pat. No. 6,858,211 which is the national stage under § 371 of PCT Application No. PCT/US98/14976, filed Jul. 20, 1998, published in English under PCT Article 21(2). The parent application is incorporated herein by reference in its entirety.

FIELD OF THE INVENTION

This invention relates to conjugates of the O-specific polysaccharide of Shiga toxin-producing bacteria, such as *E. coli* O157, with carrier, and compositions thereof, and to methods of using of these conjugates and/or compositions thereof for eliciting an immunogenic response in mammals, including responses which provide protection against, or reduce the severity of, bacterial infections. More particularly it relates to the use of polysaccharides containing the tetrasaccharide repeat unit: (→3)-α-D-GalpNAc-(1→2)-α-D-PerpNAc-(1→3)-α-L-Fucp-(1→4)-β-D-Glcp-(1→), and conjugates thereof, to induce serum antibodies having bactericidal (killing) activity against *E. coli*, in particular *E. coli* O157. The conjugates, and compositions thereof, are useful as vaccines to induce serum antibodies which have bactericidal or bacteriostatic activity against *E. coli*, in particular *E. coli* O157, and are useful to prevent and/or treat illnesses caused by *E. coli* O157.

The invention further relates to the antibodies which immunoreact with the O-specific polysaccharide of *E. coli* O157 and/or the carrier, that are induced by these conjugates and/or compositions thereof. The invention also relates to methods and kits for detection, identification, and/or diagnosis of *E. coli* O157, using one or more of the polysaccharides, conjugates or antibodies described above.

BACKGROUND

The most successful of all carbohydrate pharmaceuticals so far have been the carbohydrate-based, antibacterial vaccines [1]. The basis of using carbohydrates as vaccine components is that the capsular polysaccharides and the O-specific polysaccharides on the surface of pathogenic bacteria are both protective antigens and essential virulence factors. The first saccharide-based vaccines contained capsular polysaccharides of *Pneumococci*: in the United States a 14-valent vaccine was licensed in 1978 followed by a 23-valent vaccine in 1983. Other capsular polysaccharides licensed for human use include a tetravalent meningococcal vaccine and the Vi polysaccharide of *Salmonella typhi* for typhoid fever. The inability of most polysaccharides to elicit protective levels of anti-carbohydrate antibodies in infants and adults with weakened immune systems could be overcome by their covalent attachment to proteins that conferred T-cell dependent properties [2]. This principle led to the construction of vaccines against *Haemophilus influenzae* b (Hib) [3] and in countries where these vaccines are routinely used, meningitis and other diseases caused by Hib have been virtually eliminated [4]. Extension of the conjugate technology to the O-specific polysaccharides of Gram-negative bacteria has provided a new generation of glycoconjugate vaccines that are undergoing various phases of clinical trials [5].

*Escherichia coli* O157:H7, an emerging infectious agent, was first recognized as a human pathogen in 1983 [6]. Diseases caused by this pathogen have subsequently been recognized worldwide [7]. Infection with *E. coli* O157 causes a spectrum of illnesses with high morbidity and mortality, ranging from watery diarrhea to hemorrhagic colitis and the extraintestinal complication of hemolytic-uremic syndrome (HUS). HUS can lead to acute renal failure requiring dialysis, and in children and infants this complication has a considerable mortality. In some studies, *E. coli* O157 was the most common cause of dysentery in patients seen in hospital clinics [8].

*E. coli* strains associated with HUS produce at least one toxin identical to the exotoxin of *Shigella dysenteriae* serotype 1, referred to herein as Shiga toxin 1 (Stx1). This toxin has been variously referred to in the literature as Vero cytotoxin 1 (VT1), Shiga-like toxin 1 (SLT-I), and Shiga toxin 1 (Stx-I or Stx1). In some cases a second toxin (variously referred to as VT2, SLT-II, Stx-II, or Stx2), structurally and functionally related to Stx1 and having a cross-reactive A subunit, is also produced. Infection with Stx-producing organisms has been correlated with HUS, and *E. coli* O157:H7 is a common serotype that produces these toxins. However, strains of *E. coli* O157 without Stx have been isolated from patients with hemorrhagic colitis.

The pathogenicity of *E. coli* O157 has been compared to that of *Shigella dysenteriae* type 1 [9, 10]. Both *E. coli* O157 and *S. dysenteriae* type 1 secrete almost identical exotoxins (Stx1 or Stx2) and cause bloody diarrhea, with its complications, only in humans. Antibiotic treatment does not ameliorate the course of enteritis caused by *E. coli* O157, and it may in fact increase the incidence of HUS caused by *E. coli* and *S. dysenteriae* type 1 [11,12]. Unlike *S. dysenteriae* type 1, which is confined to humans, *E. coli* O157:H7 lives in cattle and in other domesticated animals without causing symptoms. The feces of infected animals serve as a source of *E. coli* O157 infection in humans, through contamination of drinking water and meat.

Most adults have low or nondetectable levels of serum antibodies to *E. coli* O157 O-SP and to Shiga toxins. High levels of O-SP antibodies and low or nondetectable levels of antitoxin are regularly found following infection with *E. coli* O157 and the subsequent complication HUS. It is not known whether immunity follows infection with this pathogen.

Although there is no consensus on the host factors that might confer immunity to *E. coli* O157, the O-specific polysaccharide portion of the lipopolysaccharides of the similar genus *Shigella* have emerged as possible protective antigens [13,14]. These polysaccharides were shown to be essential for the virulence of *Shigella*, and it is now well-established that the protection is serotype specific. Since each serotype is characterized by a distinct O-specific polysaccharide, it is fair to say that protection against *E. coli* O157 is also O-specific polysaccharide specific. The safety and immunogenicity of a protein conjugate of the O-specific polysaccharides of *S. sonnei*, *S. flexneri* 2a, and *S. dysenteriae* type 1 has been demonstrated in human volunteers, and preliminary clinical trials have established the efficacy of these vaccines [9, 15, 16, 17].

The immunogenicity of saccharides, alone or as protein conjugates, is related to several variables: 1) species and the age of the recipient; 2) molecular weight of the saccharide; 3) density of the saccharide on the protein; 4) configuration of the conjugate (single vs. multiple point attachment); and 5) the immunologic properties of the protein.

Because high molecular weight polysaccharides can induce the synthesis of antibodies from B-cells alone, they are described as T-independent antigens. Three properties of polysaccharides are associated with T-independence; 1) their repetitive polymeric nature, which results in one molecule having multiple identical epitopes; 2) a minimum molecular weight that is related to their ability to adhere to and cross-link membrane-bound IgM receptors, resulting in signal transduction and antibody synthesis; and 3) resistance to degradation by mammalian enzymes. Most capsular polysaccharides are of comparatively high molecular weight ($\geqq 150$ kD), and elicit antibodies in older children and in adults but not in infants and young children. O-SPs are of lower molecular weight ($\leqq 100$ kD), and maybe considered to be haptens because they combine with antibody (are antigenic) but do not elicit antibody synthesis (are not immunogenic). The immunogenicity of O-SPs as conjugates may be explained by two factors: 1) the increase in molecular weight that allows the O-SP to adhere to a greater number of membrane-bound IgM and induce signal transduction to the B-cell; and 2) their protein component, which is catabolized by the O-SP stimulated B cell resulting in a peptide-histocompatibility II antigen signal to T cells.

Synthesis of conjugates for use as vaccines in humans has special considerations. LPS is not suitable for parenteral administration to humans because of toxicity mediated by the lipid A domain. Usually, O-SP is prepared by treatment of LPS with either acid or hydrazine in order to remove fatty acids from lipid A. The resultant products retain the core region and the O-SP with its heterogeneous range of molecular weights ($M_r$). Conjugates are prepared by schemes that bind the carrier to the O-SP at multiple sites along the O-SP, or attempt to activate one residue of the core region.

In the case of E. coli O157, vaccine development has been hindered because there is little information about mechanisms of immunity [9], and there are no valid animal models for diseases caused by E. coli O157[10].

There have been some efforts to date to attempt to obtain effective vaccine compositions against E. coli. See, e.g., Cryz et al. (U.S. Pat. No. 5,370,872), which describes the isolation of O-SP derived from LPS of 12 serotypes of E. coli and their covalent linkage to P. aeruginosa toxin A as a carrier protein [18]. The twelve monovalent conjugates were combined to form a polyvalent vaccine, which was described as being safe and immunogenic in both rabbits and humans when administered by injection. An antibody response to both the O-SP and toxin A moieties was reported, and protection of rabbits against E. coli sepsis was demonstrated upon passive immunization with the resulting IgG antibodies. However, neither bactericidal activity of the antibodies nor protection after vaccination with the conjugates was shown, and antibodies against E. coli strain O157 and protection against E. coli O157 infection are not mentioned.

Because anti-LPS or anti-O-SP antibody-mediated protection is likely to be serotype-specific, it is unlikely that the polyvalent vaccine described in U.S. Pat. No. 5,370,872 would induce a significant level of antibodies against E. coli O157 O-SP or LPS. There remains a need, therefore, for compositions and methods of inducing a significant level of antibodies against E. coli O157. There also remains a need compositions and methods for inducing antibodies which have bactericidal activity against E. coli O157, and which also prevent or ameliorate HUS.

BRIEF DESCRIPTION OF THE INVENTION

It is an object of the invention to produce antigens based on the O-specific polysaccharide of Shiga toxin-producing bacteria, particularly E. coli O157, conjugated with a carrier, and compositions thereof, and to methods of using of these conjugates and/or compositions thereof for eliciting an immunogenic response in mammals, including responses which provide protection against, or reduce the severity of, bacterial infections. More particularly, it is an object of the invention to provide conjugates having polysaccharides containing the tetrasaccharide repeat unit: (→3)-α-D-GalpNAc-(1→2)-α-D-PerpNAc-(1→3)-α-L-Fucp-(1→4)-β-D-Glcp-(1→), and compositions thereof, to induce serum antibodies having bactericidal (killing) activity against *E. coli*, in particular *E. coli* O157. The conjugates, and compositions thereof, are useful as vaccines to induce serum antibodies which have bactericidal or bacteriostatic activity against *E. coli*, in particular *E. coli* O157, and are useful to prevent and/or treat illnesses caused by *E. coli* O157.

It is yet another object of the present invention to provide conjugates of *E. coli* O157 O-SP bound to the non-toxic B-subunit of Shiga toxin 1 (StxB1), or mutated non-toxic holotoxin of Shiga toxin 1 or Shiga toxin 2. These conjugates have the advantage of inducing both (1) serum IgG anti-O157-LPS with bactericidal activity, and (2) neutralizing antibodies to Shiga toxin 1 or Shiga toxin 2 (Stx1 or Stx2)[19,20,21].

It is also an object of the invention to provide antibodies which immunoreact with the O-specific polysaccharide of *E. coli* O157 and/or the carrier, that are induced by these conjugates and/or compositions thereof. Such antibodies may be isolated, or may be provided in the form of serum containing these antibodies.

It is also an object of the invention to provide a method for the treatment or prevention of *E. coli* O157 infection in a mammal, by administration of compositions containing the antibodies of the invention, or serum containing the antibodies of the invention.

The invention also provides methods and kits for identifying, detecting, and/or diagnosing *E. coli* O157 infection or colonization using the antibodies which immunoreact with the O-specific polysaccharide of *E. coli*. The invention also relates to methods and kits for identifying, detecting and/or diagnosing the presence of Shiga toxins 1 or 2.

DETAILED DESCRIPTION OF THE INVENTION

The invention provides conjugates of an *E. coli* O157 O-specific polysaccharide covalently bound, either directly or through a linker, to a carrier, and compositions thereof. The present invention also encompasses mixtures of such conjugates and compositions thereof. In a preferred embodiment, the carrier is the non-toxic B subunit of Shiga toxin 1 or 2 (StxB1, StxB2), or a non-toxic mutant of Stx1 or Stx2 holotoxin. In yet another preferred embodiment, the particular *E. coli* O157-Stx conjugate is part of a composition containing O-SP-carrier conjugates from other *E. coli* strains that commonly cause HUS, to form a multivalent vaccine for broad coverage against HUS. Hyperimmune plasma containing both anti-LPS and neutralizing antibodies to Stxs are expected to provide protective and therapeutic effects in at-risk individuals and in patients during outbreaks.

The invention also provides methods of using these conjugates or compositions thereof to induce in mammals, in particular, humans, the production of antibodies which immunoreact with the O-specific polysaccharide of *E. coli* O157. In the preferred embodiment, antibodies which immunoreact with Shiga toxin 1 or Shiga toxin 2 are also produced. The antibodies which immunoreact with the O-specific polysaccharide of *E. coli* O157 are useful for the identification, detection, and/or diagnosis of *E. coli* O157 colonization and/or infection. Antibodies which have bactericidal or bacteriostatic activity against *E. coli* O157 are useful to prevent and/or treat illnesses caused by *E. coli* O157. Antibodies which immunoreact with Shiga toxins 1 and 2 are useful to neutralize Shiga toxins 1 and 2, and either decrease the incidence and/or severity of hemolytic-uremic syndrome, or prevent the increase of its incidence and/or severity, in established infections.

Pharmaceutical compositions of this invention are capable, upon injection into a human of an amount containing 25 µg of *E. coli* O157 O-specific polysaccharide, of inducing in the serum bactericidal activity against *E. coli* O157, such that the serum kills, in the presence of complement, 50% or more of *E. coli* O157 at a serum dilution of 1300:1 or more. Preferred compositions can induce serum bactericidal activity against *E. coli* O157 such that the serum kills 50% or more of *E. coli* O157 at a serum dilution of 32,000:1 or more, and the most preferred compositions can induce serum bactericidal activity against *E. coli* O157 such that the serum kills 50% or more of *E. coli* O157 at a serum dilution of 64,000:1 or more. The O-SP conjugate vaccines of this invention are designed to induce serum IgG antibodies that will inactivate an inoculum of *E. coli* O157 at the entrance of the jejunum before an infection is established.

The invention also provides a saccharide-based vaccine, which is intended for active immunization for prevention of *E. coli* O157 infection, and for preparation of immune antibodies as a therapy, preferably for established infections. The vaccines of this invention are designed to confer specific preventative immunity against infection with *E. coli* O157, and to induce antibodies specific to *E. coli* O157 O-SP and LPS. The *E. coli* O157 vaccine is composed of non-toxic bacterial components, suitable for infants, children of all ages, and adults.

The conjugates of this invention, and/or compositions thereof, as well as the antibodies thereto, will be useful in increasing resistance to, preventing, ameliorating, and/or treating *E. coli* O157 infection in humans, and in reducing or preventing *E. coli* O157 colonization in humans.

This invention also provides compositions, including but not limited to, mammalian serum, plasma, and immunoglobulin fractions, which contain antibodies which are immunoreactive with *E. coli* O157 O-SP, and which preferably also contain antibodies which are immunoreactive with Shiga toxins 1 or 2, in particular with the B subunit of Shiga toxins 1 or 2. These compositions, in the presence of complement, have bacteriostatic or bactericidal activity against *E. coli* O157. These antibodies and antibody compositions are useful to prevent, treat, or ameliorate infection and disease caused by the microorganism. The invention also provides such antibodies in isolated form.

High titer anti-O157 sera, or antibodies isolated therefrom, could be used for therapeutic treatment for patients with *E. coli* O157 infection or hemolytic-uremic syndrome (HUS). Antibodies elicited by the O-SP conjugates of this invention may be used for the treatment of established *E. coli* O157 infections, and are also useful in providing passive protection to an individual exposed to *E. coli* O157.

The present invention also provides diagnostic tests and/or kits for *E. coli* O157 infection and/or colonization, using the conjugates and/or antibodies of the present invention, or compositions thereof.

The present invention also provides an improved method for synthesizing an O-SP peptide conjugate, particularly the *E. coli* O157 O-SP conjugated to the B subunit of Shiga toxin 1 or 2 (Stx1 or Stx2), or to a mutant, non-toxic Stx1 or Stx2 holotoxin.

A number of primary uses for the conjugates of this invention are envisioned. The *E. coli* LPS-protein conjugates of this invention, and the antibodies they induce, are expected to be useful for several purposes, including but not limited to:

1) a vaccine for high-risk groups (children under 5 and senior citizens);
2) high-titered globulin for plasmapheresis, for prophylaxis and treatment of *E. coli* O157-infected patients; and
3) diagnostic reagents for detecting and/or identifying *E. coli* O157.

The invention is intended to be included in the routine immunization schedule of infants and children, and in individuals at risk for *E. coli* O157 infection. It is also planned to be used for intervention in epidemics caused by *E. coli* O157. Additionally, it is may be used as a component of a multivalent vaccine for *E. coli* O157 and other enteric pathogens, useful for example for the routine immunization of infants. The invention is also intended to prepare antibodies with bacteriostatic bactericidal activity toward *E. coli* O157, for therapy of established infection. The invention is also intended to provide a diagnostic test for *E. coli* O157 infection and/or colonization.

Definitions

Galp=galactosaminopyranosyl; Perp=perosaminopyranosyl; Fucp=fucopyranosyl; Glcp=glucopyranosyl.

As used herein, the term "O-SP" when used alone refers generically to O-specific polysaccharide, whether produced by acidolysis or hydrazinolysis of lipopolysaccharide. When used in designating conjugates, however (e.g. O-SP-rEPA, DeA-LPS-rEPA, etc.) these products are differentiated by use of the term "O-SP" for O-specific polysaccharide produced by acidolysis, and the term "DeA-LPS" for O-specific polysaccharide produced by hydrazinolysis.

As used herein, the terms "immnunoreact" and "immunoreactivity" refer to specific binding between an antigen or antigenic determinant-containing molecule and a molecule having an antibody combining site, such as a whole antibody molecule or a portion thereof.

As used herein, the term "antibody" refers to immunoglobulin molecules and immunologically active portions of immunoglobulin molecules. Exemplary antibody molecules are intact immunoglobulin molecules, substantially intact immunoglobulin molecules and portions of an immunoglobulin molecule, including those portions known in the art as Fab, Fab', F(ab')$_2$ and F(v), as well as chimeric antibody molecules.

Polymeric Carriers

Carriers are chosen to increase the immunogenicity of the polysaccharide and/or to raise antibodies against the carrier which are medically beneficial. Carriers that fulfill these criteria are described in the art [22, 23, 24, 25]. A polymeric carrier can be a natural or a synthetic material containing one or more functional groups, for example primary and/or secondary amino groups, azido groups, or carboxyl groups. The carrier can be water soluble or insoluble.

Water soluble peptide carriers are preferred, and include but are not limited to natural or synthetic polypeptides or proteins, such as bovine serum albumin, and bacterial or viral proteins or non-toxic mutants or polypeptide fragments thereof, e.g., tetanus toxin or toxoid, diphtheria toxin or toxoid, *Pseudomonas aeruginosa* exotoxin or toxoid, recombinant *Pseudomonas aeruginosa* exoprotein A, pertussis toxin or toxoid, *Clostridium perfringens* and *Clostridium welchii* exotoxins or toxoids, mutant non-toxic Shiga toxin holotoxin, Shiga toxins 1 and 2, the B subunit of Shiga toxins 1 and 2, and hepatitis B surface antigen and core antigen.

Examples of water insoluble carriers include, but are not limited to, aminoalkyl SEPHAROSE, e.g., aminopropyl or aminohexyl SEPHAROSE (Pharmacia Inc., Piscataway, N.J.), aminopropyl glass, and the like. Other carriers may be used when an amino or carboxyl group is added, for example through covalent linkage with a linker molecule.

Methods for Attaching Polymeric Carriers

Methods for binding a polysaccharide to a protein are well known in the art. For example, a polysaccharide containing at least one carboxyl group, through carbodiimide condensation, may be thiolated with cystamine, or aminated with adipic dihydrazide, diaminoesters, ethylenediamine and the like. Groups which can be introduced by such known methods include thiols, hydrazides, amines and carboxylic acids. Thiolated and aminated intermediates are stable, and may be freeze dried and stored cold. Thiolated intermediates may be covalently linked to a polymeric carrier containing a sulfhydryl group, such as a 2-pyridyldithio group. Aminated intermediates may be covalently linked to a polymeric carrier containing a carboxyl group through carbodiimide condensation. See for example reference [26], where 3 different methods for conjugating *Shigella* O-SP to tetanus toxoid are exemplified. Because the methods of the present invention better preserve the native structure of the antigen, they are preferred over methods which oxidize the polysaccharide with periodate [18].

The polysaccharide can be covalently bound to a carrier with or without a linking molecule. To conjugate without a linker, for example, a carboxyl-group-containing polysaccharide and an amino-group-containing carrier are mixed in the presence of a carboxyl activating agent, such as a carbodiimide, in a choice of solvent appropriate for both the polysaccharide and the carrier, as is known in the art [25]. The polysaccharide is often conjugated to a carrier using a linking molecule. A linker or crosslinking agent, as used in the present invention, is preferably a small linear molecule having a molecular weight of about 500 or less, and is non-pyrogenic and non-toxic in the final product form, for example as disclosed in references [22-25].

To conjugate with a linker or crosslinking agent, either or both of the polysaccharide and the carrier may be covalently bound to a linker first. The linkers or crosslinking agents are homobifunctional or heterobifunctional molecules, e.g., adipic dihydrazide, ethylenediamine, cystamine, N-succinimidyl 3-(2-pyridyldithio)propionate (SPDP), N-succinimidyl-N-(2-iodoacetyl)-β-alaninate-propionate (SIAP), succinimidyl 4-(N-maleimido-methyl)cyclohexane-1-carboxylate (SMCC), 3,3'-dithiodipropionic acid, and the like. Also among the class of heterobifunctional linkers area omega-hydroxy and omega-amino alkanoic acids.

More specifically, attachment of the *E. coli* O157 O-specific polysaccharide to a protein carrier can be accomplished by methods known to the art. In a preferred embodiment, the attachment is accomplished by first cyanating the O-specific polysaccharide with a cyanylation reagent, such as cyanogen bromide, N-cyano-N,N,N-triethylammonium tetrafluoroborate, 1-cyano-4-(N,N-dimethylamino)pyridine tetrafluoroborate, or the like. Several such cyanylation reagents are known to those skilled in the art [27]. The resulting cyanated *E. coli* O157 O-specific polysaccharide may then be reacted with a linker, such as a dicarboxylic acid dihydrazide, preferably adipic acid dihydrazide, so as to form a hydrazide-functionalized polysaccharide. This hydrazide-functionalized polysaccharide is then coupled to the carrier protein by treatment with a peptide coupling agent, preferably a water-soluble carbodiimide such as 1-ethyl-3-(3-dimethylaminopropyl)carbodiimide, 1-ethyl-3-(3-dimethylaminopropyl)-carbodiimide methiodide, or the like.

More preferably, the cyanated *E. coli* O157 O-specific polysaccharide is directly reacted with the carrier protein, without introduction of a linker. It has been found, surprisingly, that, in the exemplified conjugates, elimination of the customary linker provides a more effective immunogen in the case of the *E. coli* O157 O-specific polysaccharide.

Regardless of the precise method used to prepare the conjugate, after the coupling reactions have been carried out the unbound materials are removed by routine physicochemical methods, such as for example gel filtration or ion exchange column chromatography, depending on the materials to be separated. The final conjugate consists of the polysaccharide and the carrier bound directly or through a linker.

Dosage for Vaccination

The present inoculum contains an effective, immunogenic amount of a polysaccharide-carrier conjugate of this invention. The effective amount of polysaccharide-carrier conjugate per unit dose sufficient to induce an immune response to *E. coli* O157 depends, among other things, on the species of mammal inoculated, the body weight of the mammal, and the chosen inoculation regimen, as is well known in the art. Inocula typically contain polysaccharide-carrier conjugates with concentrations of polysaccharide from about 1 micrograms to about 10 milligrams per inoculation (dose), preferably about 3 micrograms to about 100 micrograms per dose, and most preferably about 5 micrograms to 50 micrograms per dose.

The term "unit dose" as it pertains to the inocula refers to physically discrete units suitable as unitary dosages for mammals, each unit containing a predetermined quantity of active material (polysaccharide) calculated to produce the desired immunogenic effect in association with the required diluent.

Inocula are typically prepared as solutions in physiologically tolerable (acceptable) diluents such as water, saline, phosphate-buffered saline, or the like, to form an aqueous pharmaceutical composition. Adjuvants, such as aluminum hydroxide, may also be included in the compositions.

The route of inoculation may be intramuscular, subcutaneous or the like, which results in eliciting antibodies protective against *E. coli* O157. In order to increase the antibody level, a second or booster dose may be administered approximately 4 to 6 weeks after the initial injection. Subsequent doses may be administered as indicated herein, or as desired by the practitioner.

Antibodies

An antibody of the present invention in one embodiment is characterized as comprising antibody molecules that immunoreact with *E. coli* O157 O-SP or LPS.

An antibody of the present invention is typically produced by immunizing a mammal with an immunogen or vaccine containing an *E. coli* O157 polysaccharide-protein carrier conjugate to induce, in the mammal, antibody molecules having immunospecificity for the immunizing polysaccharide. Antibody molecules having immunospecificity for the protein carrier, such as the B subunit of Shiga toxins 1 or 2, will also be produced. The antibody molecules may be collected from the mammal and, optionally, isolated and purified by methods known in the art.

Human or humanized monoclonal antibodies are preferred, including those made by phage display technology, by hybridomas, or by mice with human immune systems. The antibody molecules of the present invention may be polyclonal or monoclonal. Monoclonal antibodies may be produced by methods known in the art. Portions of immunoglobulin molecules, such as Fabs, may also be produced by methods known in the art.

The antibody of the present invention may be contained in blood plasma, serum, hybridoma supernatants and the like. Antibody-containing serum of this invention will be capable of killing, in the presence of complement, 50% of E. coli O157 at a serum dilution of 1300:1 or more, preferably will do so at a dilution of 32,000:1 or more, and most preferably will be capable of killing 50% of E. coli O157 at a dilution of 64,000:1 or more.

Alternatively, the antibodies of the present invention are isolated to the extent desired by well known techniques such as, for example, ion chromatography or affinity chromatography. The antibodies may be purified so as to obtain specific classes or subclasses of antibody such as IgM, IgG, IgA, $IgG_1$, $IgG_2$, $IgG_3$, $IgG_4$ and the like. Antibodies of the IgG class are preferred for purposes of passive protection. The antibodies of the present invention have a number of diagnostic and therapeutic uses. The antibodies can be used as an in vitro diagnostic agents to test for the presence of E. coli O157 in biological samples or in meat and meat products, in standard immunoassay protocols. Such assays include, but are not limited to, agglutination assays, radioimmunoassays, enzyme-linked immunosorbent assays, fluorescence assays, Western blots and the like. In one such assay, for example, the biological sample is contacted with first antibodies of the present invention, and a labeled second antibody is used to detect the presence of E. coli O157 to which the first antibodies have bound.

Such assays may be, for example, of direct format (where the labeled first antibody is reactive with the antigen), an indirect format (where a labeled second antibody is reactive with the first antibody), a competitive format (such as the addition of a labeled antigen), or a sandwich format (where both labeled and unlabelled antibody are utilized), as well as other formats described in the art.

The antibodies of the present invention are also useful in prevention and treatment of infections and diseases caused by E. coli O157.

In providing the antibodies of the present invention to a recipient mammal, preferably a human, the dosage of administered antibodies will vary depending upon such factors as the mammal's age, weight, height, sex, general medical condition, previous medical history and the like.

In general, it is desirable to provide the recipient with a dosage of antibodies which is in the range of from about 1 mg/kg to about 10 mg/kg body weight of the mammal, although a lower or higher dose may be administered. The antibodies of the present invention are intended to be provided to the recipient subject in an amount sufficient to prevent, or lessen or attenuate the severity, extent or duration of the infection by E. coli O157. Antibodies which immunoreact with Shiga toxin 1 or 2 are intended to be provided to the recipient subject in an amount sufficient to prevent, or lessen or attenuate the severity, extent or duration of the infection by Shigatoxin producing organisms, such as E. coli strains O157, O111, O26, and O17.

The administration of the agents of the invention may be for either "prophylactic" or "therapeutic" purpose. When provided prophylactically, the agents are provided in advance of any symptom. The prophylactic administration of the agent serves to prevent or ameliorate any subsequent infection. When provided therapeutically, the agent is provided at (or shortly after) the onset of a symptom of infection. The agent of the present invention may, thus, be provided prior to the anticipated exposure to E. coli O157 (or other Shiga toxin producing bacteria), so as to attenuate the anticipated severity, duration or extent of an infection and disease symptoms, after exposure or suspected exposure to these bacteria, or after the actual initiation of an infection.

For all therapeutic, prophylactic and diagnostic uses, the polysaccharide-carrier conjugates of this invention, as well as antibodies and other necessary reagents and appropriate devices and accessories may be provided in kit form so as to be readily available and easily used.

The following examples are exemplary of the present processes and incorporate suitable process parameters for use herein. These parameters may be varied, however, and the following should not be deemed limiting.

EXAMPLES

Example 1

Conjugation of E. coli O157 O-SP with Various Polypeptides

O157 LPS were detoxified by hydrolysis with acetic acid (designated O-SP) or with hydrazine (designated DeA-LPS) and then covalently bound to Clostridium welchii exotoxin C (Pig Bel toxoid [CW]), Pseudomonas aeruginosa recombinant exoprotein A (rEPA), or bovine serum albumin (BSA) [8]. These E. coli O157:H7 polysaccharide-protein conjugates were given the following designations:

$O\text{-}SP\text{-}BSA_1$
$O\text{-}SP\text{-}BSA_2$
DeA-LPS-BSA
O-SP-CW
DeA-LPS-CW
O-SP-rEPA
$DeA\text{-}LPS\text{-}rEPA_1$
$DeA\text{-}LPS\text{-}rEPA_2$ Mice were immunized with these conjugate compositions containing 2.5 ug of polysaccharide, with booster injections, and the determination of antibody levels and bactericidal antibody titers in mice were determined. Geometric mean antibody level (ELISA units) and immunoglobulin class composition of LPS antibodies elicited by E. coli O157-rEPA conjugates in mice are shown in Table 1.

TABLE 1

Immunoglobulin class composition of LPS antibodies elicited by E. coli O157-rEPA conjugates in mice

| | Geometric mean antibody level (ELISA units) ($25^{th}$-$75^{th}$ centiles) | | |
|---|---|---|---|
| Immunogen | After $1^{st}$ injection | After $2^{nd}$ injection | After $3^{rd}$ injection |
| | IgG | | |
| O-SP-rEPA | 0.08 (0.05-0.10) | 2.50* (1.06-4.79) | 6.26** (3.37-9.6) |
| DeA-LPS-$rEPA_1$ | 0.07 (0.04-0.13) | 1.37* (0.50-2.63) | 4.49*** (1.49-16.4) |

TABLE 1-continued

Immunoglobulin class composition of LPS antibodies elicited by
E. coli O157-rEPA conjugates in mice

| Immunogen | Geometric mean antibody level (ELISA units) (25th-75th centiles) | | |
|---|---|---|---|
| | After 1st injection | After 2nd injection | After 3rd injection |
| DeA-LPS-rEPA$_2$ | 0.07 (0.06-0.07) | 0.66* (0.07-3.73) | 5.10** (2.23-10.0) |
| | IgM | | |
| O-SP-rEPA | 0.53 (0.36-0.72) | 0.51 (0.31-1.12) | 0.38 (0.22-0.59) |
| DeA-LPS-rEPA$_1$ | 0.11 (0.04-0.34) | 0.32 (0.08-0.89) | 0.94 (0.28-2.94) |
| DeA-LPS-rEPA$_2$ | 0.09 (0.06-0.11) | 0.32 (0.06-1.53) | 0.28 (0.21-0.45) | a. IgG and IgM components of the hyperimmune O157 sera (see Materials and Methods) were used as standards and assigned a value of 100 ELISA U each. Injection of O-SP, DeA-LPS, or saline did not elicit detectable antibodies.
*$P < 0.01$ when compared with the value for O-SP-rEPA after the first injection;
**$P > 0.02$ when compared with the value for the same immunogen after the second injection;
***$P < 0.07$ when compared with the value for the same immunogen after the second injection.

Bactericidal activity of serum LPS antibodies elicited in mice by immunization with heat-killed E. coli O157:H7 or O-specific polysaccharide-protein conjugates are shown in Table 2 below:

TABLE 2

Bactericidal activity of serum LPS antibodies elicited in mice by immunization with heat-killed E. coli O157:H7 or O-specific polysaccharide-protein conjugates

| Vaccine[a] | Antibody titer (ELISA units) | | | Reciprocal bacterial titer[b] |
|---|---|---|---|---|
| | Total | IgG | IgM | |
| Expt 1 | | | | |
| O-SP-CW | 79.25 | | | 100 |
| DeA-LPS-CW | 15.1 | | | >100 |
| DeA-LPS-CW | 19.4 | | | 80 |
| E. coli O157:H7 | 100.0 | | | 35 |
| Expt 2 | | | | |
| DeA-LPS-rEPA | | 18.8 | 0.07 | 320 |
| DeA-LPS-rEPA | | 56.8 | 0.33 | 640 |
| DeA-LPS-rEPA | | 32.8 | 0.45 | 640 |
| O-SP-rEPA | | 18.6 | 0.44 | 640 |
| O-SP-rEPA | | 15.8 | 0.59 | 640 |

[a]E. coli O157:H7 is pooled hyperimmune sera from mice injected with heat-killed E. coli O157. All other sera were from individual mice taken after the third conjugate injection. Serum dilutions were mixed with an equal volume of ~$10^3$ E. coli O157:H7 organisms per ml and complement.
[b]The reciprocal bactericidal titer is expressed as the highest serum dilution yielding 50% killing. Absorption with LPS or DeA-LPS removed all of the bactericidal activity from sera from conjugate-injected mice and 90% from the hyperimmune sera prepared by injection of heat-killed E. coli O157.

Example 2

Conjugation of E. coli O157 O-SP with rEPA: Preparation of Vaccine Compositions

As discussed above, O-SP of E. coli O157, prepared by acetic acid hydrolysis, and DeA-LPS O157, prepared by hydrazinolysis, have been previously described. Conjugates of these polysaccharides to rEPA (O-SP O157-rEPA, DeA-LPS O157-$_1$, and DeA-LPS O157-rEPA$_2$) were prepared by the published procedure [8]. These conjugates were approved for investigation by the NIH (OH94-CH-N040), the FDA (BB-IND-5528) and the Institutional Review Board, Carolinas Medical Center, Charlotte, N.C. (08-94-08B). Pyrogen, sterility and safety testing of the final containers were performed by the Center for Biologics Evaluation and Research, FDA. All three conjugates elicited serum IgG anti-LPS with bactericidal activity when injected by a clinically relevant scheme and dosage in mice[8].

Clinical Protocol

Volunteers of either gender and any ethnic group between ages 18 and 44 years were recruited from the staff of Carolinas Health Care System and the city of Charlotte, N.C. Exclusion criteria were: pregnancy or planned pregnancy in the next six months, positive stool culture for E. coli O157 or a history of hemorrhagic colitis, chronic disease including HIV 1, hepatitis or inflammatory bowel disease, acute illness including diarrhea, taking controlled substances, hospitalization within the year, taking regular medications, participation in another research protocol during the next two months, abnormal liver function test or having received cholera vaccine [32, 28]. After giving Informed Consent, a medical history and physical examination were performed and blood was obtained for assay of HIV 1, hepatitis b surface antigen, pregnancy test, liver function tests (LFT), antibodies to E. coli O157 LPS and P. aeruginosa exotoxin A (ETA) and a culture of the stool for E. coli O157. Eighty-seven volunteers were determined healthy and randomized into 3 groups of 29 to receive a injection of 0.5 ml of one of the experimental vaccines containing 25 μg of O-SP. Injections were delivered intramuscularly into the deltoid muscle. The volunteers were observed for 30 minutes after vaccination. Temperature and local or systemic reactions were recorded at 6, 24, 48 and 72 hours following vaccination.

All volunteers returned at 1, 4 and 26 weeks following vaccination for a health history and reaction, and blood was drawn. LFTs were performed, total protein/albumin), total bilirubin/direct and indirect, alkaline phosphatase (AP), SGOT (AST), SGPT (ALT), and GGT at each visit. Volunteers who had abnormal LFT levels at one week had repeated LFT tests at subsequent visits. Serum was collected for LPS and ETA antibody assays. Stool cultures for E. coli O157 were obtained prior to and 4 and 26 weeks following vaccination. E. coli O157 LPS and P. aeruginosa exotoxin A (ETA) antibodies of the volunteers were determined by ELISA [8].

Statistical Methods

Antibody levels are expressed as geometric means (GM). Levels below the sensitivity of ELISA were assigned the value of one-half of that level. Comparison of GM was performed with either the two-sided t-test, paired t-test or the Wilcoxon test where appropriate.

Results—Clinical Responses

One volunteer reported 3-6 cm diameter of erythema at the injection site within 24 hours following vaccination; one reported 1-3 cm and one reported >6 cm. Four volunteers reported erythema and induration after 72 hours observation: one (1-3 cm), two (3-6 cm) and one (>6 cm); all erythemas resolved by the 17th day.

Six volunteers (6.9%) had asymptomatic elevations (up to 35% above the normal range) of one or more serum LFT following vaccination. Four of these 6 volunteers had mild elevation of LDH and/or AP that returned to normal at 4-5 weeks. One volunteer had a serum bilirubin of 2.2 mg/dl (normal 1.5 mg/dl) with indirect bilirubin of 1.9 mg/dl at four weeks, and normal values at 14 weeks. Another volunteer had ALT (SGPT) and GGT evaluations of 33% and 26% respectively at four weeks, and elevations 13% and 47% respectively at 24 weeks following vaccination.

Ninety percent of volunteers reported oral temperatures less than 37.2° C. at different observation times post-vaccination. The remainder of the volunteers reported oral temperatures 37.2-38° C. with symptoms of acute respiratory infections.

There was no significant correlation between the reported post-vaccination observations and the lots of vaccine administered and no volunteer was hospitalized during the study.

One recipient of DeA-LPS O157-rEPA$_1$ had a stool culture positive for E. coli O157 at the 1 week post-vaccination visit. This volunteer had no adverse reactions following vaccination, and no complaints throughout the study, and subsequent stool cultures were negative for E. coli O157.

Results—Antibody Levels (Tables 3a and 3b)

IgG: Pre-vaccination GM IgG anti-LPS levels in the three groups were low and similar. One week after vaccination, 71/87 (82%) responded with a ≧4-fold rise. Four weeks after vaccination, there were further rises in GM levels in all three groups (p<0.0001): all vaccinees responded with a ≧4-fold rise over the 1 week level. The GM levels in recipients of O-SP-rEPA were slightly higher than in those injected with either of the two DeA-LPS-rEPA conjugates (61.9 vs. 46.3 NS, 61.9 vs. 36.3, p<0.05). At 26 weeks, the GM levels of the 3 groups were similar (32.8, 31.2, 33.1, NS). Although the decline from the four week level was significant for each group (p<0.05), the levels at 26 weeks were higher than those at one week following vaccination in all three groups (32.8, 31.2, 33.1 vs. 7.93, 5.73, 4.12, p<0.01); and 97% of volunteers had ≧10-fold higher levels at 26 weeks than their pre-injection levels. Within the 25-75 percentile range, geometric mean titers were increased 68-fold to 132-fold after 4 weeks, and the overall result for the three conjugates at 4 weeks was a 93-fold increase in geometric mean titer. At 26 weeks, the results were increases of 61-fold to 70-fold, and 64-fold increase overall for all conjugates. The volunteer who had a stool culture positive for E. coli O157 at 1 week had IgG anti-LPS levels at pre-immunization, 1-, 4-, and 26-week post-immunization of 0.81, 1.15, 7.73 and 7.01 respectively, that are lower than the GM of all 3 groups.

IgM: Each conjugate elicited a significant rise in IgM anti-LPS at the 4 and 26 weeks intervals (p<0.0001). O-SP-rEPA elicited the highest level at each post vaccination interval but the difference was significant only at 4 weeks (32.8 vs. 18.1,19.1, p<0.05). At the 4 week interval, there was a ≧4-fold rise in 61/87 (70%) and in 34/86 (39.5%) at 26 weeks compared to pre-vaccination levels. There was a significant decrease in serum IgM anti-LPS at 26 weeks in all of the three groups (p<0.02) but there were no significant differences in the GM levels among the three groups. The volunteer who had a stool culture positive for E. coli O157 at 1 week had a pre-immunization anti-LPS IgM level which was relatively high (11.9). The IgM levels declined 1, 4 and 26 weeks post-immunization (7.04, 10.6 and 5.94 units, respectively). These levels are lower than the GM of the three groups.

IgA: Pre-vaccination levels of IgA anti-LPS were low. Similar to IgG and IgM anti-LPS, about 90% of the volunteers responded with ≧4-fold rise in IgA anti-LPS at one week, and 99% at four weeks (p<0.001). IgA anti-LPS GM levels declined to about 70% of the levels at the 4 week interval.

TABLE 3a

Geometric mean titers of serum IgG, IgM, and IgA lipopolysaccharide (LPS) antibodies elicited in volunteers by injection of E. coli O157 O-SP-rEPA conjugates.

| Conjugate | ELISA units (25$^{th}$-75$^{th}$ percentiles) | | | |
|---|---|---|---|---|
| | Preimmune | 1 Week | 4 Weeks | 26 Weeks |
| | IgG | | | |
| O-SP-rEPA | 0.47 (0.3-0.7) | 7.93 (2.8-24) | 61.9 (40-91) | 32.8 (23-50) |
| DeA-LPS-rEPA$_1$ | 0.51 (0.3-0.9) | 5.73 (1.8-22) | 46.3 (22-84) | 31.2 (12-61) |
| DeA-LPS-rEPA$_2$ | 0.54 (0.3-0.9) | 4.12 (2.2-6.0) | 36.6 (20-76) | 33.1 (15-57) |
| | IgM | | | |
| O-SP-rEPA | 8.10 (4.0-14) | 32.8 (23.51) | 64.7 (47-109) | 28.6 (17-44) |
| DeA-LPS-rEPA$_1$ | 7.19 (3.1-12) | 19.1 (9.2-29) | 43.5 (13-56) | 22.5 (11-34) |
| DeA-LPS-rEPA$_2$ | 7.41 (4.6-13) | 18.1 (10-27) | 42.7 (26-73) | 25.3 (17-35) |
| | IgA | | | |
| O-SP-rEPA | 0.06 (0.0-0.1) | 0.98 (0.5-2.4) | 1.73 (1.0-2.5) | 1.17 (0.9-2.1) |
| DeA-LPS-rEPA$_1$ | 0.06 (0.0-0.1) | 0.58 (0.3-0.8) | 1.26 (0.6-3.7) | 1.01 (0.5-1.9) |
| DeA-LPS-rEPA$_2$ | 0.07 (0.0-0.1) | 0.90 (0.4-1.8) | 2.13 (1.2-4.9) | 1.40 (1.0-2.5) |

NOTE:
High-titered postvaccination sera were used as standards. IgG, IgM, and IgA were assigned value of 100 ELISA units. Each group had 29 volunteers.

TABLE 3b

Fold increases in geometric mean titers of serum IgG, IgM, and IgA lipopolysaccharide (LPS) antibodies elicited in volunteers.

| Ab class | Conjugate | -fold increase in 25$^{th}$-75$^{th}$ percentiles | | |
|---|---|---|---|---|
| | | 1 Week | 4 Weeks | 26 Weeks |
| IgG | O-SP-rEPA | 17 | 132 | 70 |
| | DeA-LPS-rEPA$_1$ | 11 | 91 | 61 |
| | DeA-LPS-rEPA$_2$ | 7.6 | 68 | 61 |
| | Geometric mean | 11 | 93 | 64 |
| IgM | O-SP-rEPA | 4.0 | 8.0 | 3.5 |
| | DeA-LPS-rEPA$_1$ | 2.7 | 6.0 | 3.1 |
| | DeA-LPS-rEPA$_2$ | 2.4 | 5.8 | 3.4 |
| | Geometric Mean | 3.0 | 6.5 | 3.3 |

TABLE 3b-continued

Fold increases in geometric mean titers of serum IgG, IgM, and IgA lipopolysaccharide (LPS) antibodies elicited in volunteers.

| Ab class | Conjugate | –fold increase in 25th-75th percentiles | | |
|---|---|---|---|---|
| | | 1 Week | 4 Weeks | 26 Weeks |
| IgA | O-SP-rEPA | 16 | 29 | 20 |
| | DeA-LPS-rEPA$_1$ | 9.7 | 21 | 17 |
| | DeA-LPS-rEPA$_2$ | 13 | 30 | 20 |
| | Geometric Mean | 13 | 26 | 19 |

NOTE:
High-titered postvaccination sera were used as standards. IgG, IgM, and IgA were assigned value of 100 ELISA units. Each group had 29 volunteers.

Results—Serum Bactericidal Activity (Table 4)

Serum from high-responding volunteers (above the 75th percentile) was diluted serially and the diluted samples were analyzed for their ability to kill *E. coli* O157:H7. Prevaccination sera had no detectable bactericidal activity against *E. coli* O157:H7. The three conjugates elicited serum bactericidal activity that roughly correlated with the serum IgG and IgM anti-LPS antibody levels.

The results in Table 4 are those for serum from high-responding volunteers. Typically, the bactericidal titer (reciprocal dilution) for 50% killing ranged from about 2400 to about 32000.

TABLE 4

Bactericidal activity (reciprocal titer) of serum anti-lipopolysaccharide (LPS) antibodies elicited in volunteers by injection of *E. coli* O157 O-SP-rEPA conjugates.

| Conjugate | Antibody level (ELISA units) | | Bactericidal titer* |
|---|---|---|---|
| | IgG | IgM | |
| Preimmune | 0.21 | 2.92 | 0 |
| Preimmune | 0.84 | 9.1 | 0 |
| O-SP-rEPA | 120.1 | 354.2 | >6.4 × 10$^4$ |
| O-SP-rEPA | 251.9 | 112.9 | 1.3 × 10$^4$ |
| O-SP-rEPA | 156.3 | 183.6 | >1.3 × 10$^3$ |
| DeA-LPS-rEPA$_1$ | 231.4 | 59.9 | >6.4 × 10$^4$ |
| DeA-LPS-rEPA$_2$ | 77.5 | 68.2 | 1.3 × 10$^4$ |

*Expressed as reciprocal of highest serum dilution yielding 50% killing.

Results—Serum anti-*P. aeruginosa* exotoxin A (Table 5)

Most volunteers had low or non-detectable ETA antibodies in their pre-vaccination sera. All three conjugates elicited significant increases in GM IgG anti-ETA at the 1-week ($p<0.002$) and 4-week ($p<0.001$) intervals. At 26 weeks, the GM levels declined to those observed one week after vaccination. There were no statistically significant differences in the GM IgG anti-ETA at each bleeding interval among the three groups.

TABLE 5

Serum antibodies to *Pseudomonas aeruginosa* exotoxin A (ETA) elicited by *Escherichia coli* O157 O-specific polysaccharide-rEPA conjugates in volunteers

| Conjugate | GM antibody level (ELISA Units*) | | | | |
|---|---|---|---|---|---|
| | n | Preimmune | 1 week | 4 weeks | 26 weeks |
| O-SP-rEPA | 29 | 0.29 | 0.93 | 1.90 | 0.88 |
| DeA-LPS-rEPA$_1$ | 29 | 0.39 | 0.91 | 1.48 | 0.87 |
| DeA-LPS-rEPA$_2$ | 29 | 0.29 | 0.65 | 0.93 | 0.67 |

*A high titered volunteer serum was used as a standard and assigned a value of 100 ELISA Units.

Example 3

Conjugation of *E. coli* O157 O-SP with STXB1 and Preparation of Vaccine Compositions

*E. coli* O157 O-SP was prepared by treatment of LPS with acetic acid as previously described [8, 9]. The B-subunit of *Shigella* toxin I (StxB1) was synthesized by *Vibrio cholerae* strain 0395-N1 (pSBC32 containing the StxB1 gene) and purified by affinity chromatography[20, 21]. SDS 7% PAGE of StxB1 showed one major band at 9 kDa and a faint band with slightly higher molecular weight.

For conjugation, O157 O-SP was bound to StxB1 directly by treatment with 1-cyano-4-dimethylaminopyridinium tetrafluoroborate (CDAP) or by carbodiimide mediated condensation with adipic acid hydrazide linker [29, 30]. For direct conjugation, CDAP (100 mg/ml in acetonitrile) was added to O-SP in saline (5 mg/ml) at 0.3/1 (wt/wt) at room temperature, pH 5.8 to 6.60 μL of 0.2 M triethylamine (TEA) added to bring the pH to 7.0 for 2 minutes. An equal weight of StxB1 was added to the CDAP treated O-SP and the pH maintained at 8.0 to 8.5 for 2 hours. The reaction mixture was passed through a 1.5×90 cm Sepharose 6B column in 0.2M NaCl, the void volume fractions collected, and designated as OSP-StxB1.

Conjugate using a linker, adipic acid dihydrazide (ADH) was prepared as described previously [8, 30]. Briefly after addition of TEA in the above procedure, an equal volume of 0.8 M ADH in 0.5 M $NaHCO_3$ was added and the pH maintained at 8.0 to 8.5 for 2 hours. The reaction mixture was dialyzed against saline overnight at 4° C. and passed through a 2.5×31 cm P10 column in water. The void volume fractions were pooled, freeze-dried, and designated as OSP-AH. OSP-AH (10 mg), dissolved in 2 ml of saline, was added to an equal weight of StxB1 and the pH brought to 5.1. The reaction mixture was put on ice and 1-ethyl-3-(3-dimethylaminopropyl)carbodiimide (EDC) was added to 0.05M and the pH maintained at 5.1 to 5.5 for 2 hours. The reaction mixture was passed through a 1.5×90 cm Sepharose 6B column in 0.2 M NaCl, the void volume fractions collected and designated as OSP-AH-StxB1. Double immunodiffusion and ELISA were performed as described [8].

Female general purpose mice (n=10/group) were injected subcutaneously with saline or one of the conjugates containing 2.5 μg saccharide on days 0, 14, and 28. The mice were exsanguinated 7 days after each injection. Pooled sera from hyperimmunized mice were used as reference and assigned 100 ELISA units for IgG and IgM respectively. Neutralization of Stx1 and Stx2 toward HeLa cells was measured using HeLa (CCL-2) cell monolayers in 96-well flat-bottom microtiter plates [21]. Each well was seeded with $1-6\times10^4$ cells in 0.1 ml. Monolayers were established by overnight incubation in 5% $CO_2$. Toxin neutralization was determined by incubating dilutions of mouse serum with Stx-I or Stx-II at a final concentration of 100 pg/ml. The serum and toxin mixture was incubated at room temperature for 30 minutes and 0.1 ml was added to each well. Following incubation overnight, the surviving cells were determined spectro-photometrically using the crystal violet staining method of Gentry and Dalrymple[31]. Toxin neutralization was determined from a dose response curve of either Shiga toxin on each 96-well plate. Bactericidal activity was assayed as described [8, 10].

Results with O157 O-SP-STXB1 Conjugates

Derivatization of O-SP with adipic acid dihydrazide was 3.1% (wt/wt), similar to previous *E. coli* O157 preparations [8]. The saccharide/protein ratios (wt/wt) were about 0.5 for both conjugates. The yields, based on saccharide in the conjugates, were 2.3% for OSP-StxB1 and 3.4% for OSP-AH-StxB1. A single line of precipitation in double immunodiffusion was formed by rabbit anti-Stx1 and mouse hyperimmune anti-O157 reacted against either conjugate.

After three injections, both conjugates elicited statistically significant rises of IgG and IgM anti-LPS (Table 6). The geometric mean (GM) anti-LPS level elicited by OSP-StxB1 was 0.63 for IgG and 0.14 for IgM and for O-SP-AH-StxB1 were 1.7 for IgG and 0.25 for IgM: the differences between two conjugates were not statistically significant.

TABLE 6

Geometric mean IgG and IgM serum LPS antibody levels and neutralization titers against Shiga toxin 1 elicited in mice by conjugates of *Escherichia coli* O157 O-SP with StxB1.

| | Anti-LPS (ELISA)* | | Neutralization Titer (%)† Serum Dilution | | |
|---|---|---|---|---|---|
| Immunogen | IgG | IgM | 1:100 | 1:1000 | 1:10,000 |
| Saline | <0.05 | <0.05 | 0‡ | 0 | 0 |
| OSP-AH-StxB1 | 1.7 | 0.25 | >99 | 90 | 34 |
| OSP-StxB1 | 0.63 | 0.14 | >99 | 98 | 70 |

*Geometric mean of sera from 10 mice. Expressed in ELISA units using pooled hyperimmune mouse sera as reference (100 units for IgG and IgM respectively).

†Geometric mean (n = 10) neutralization titer determined with Stx1 and HeLa cells, ‡No neutralization at 1/100 dilution.

Sera from mice injected with saline or human sera from volunteers injected with *E. coli* O157 O-SP-rEPA conjugates showed no neutralization to Stx1 or to Stx2. Sera from mice injected 3 times with either of the O157 O-SP-StxB1 conjugates showed complete neutralization of Stx1 at 1/100 dilution. At 1/1,000 dilution, the GM of neutralization titer was 90% for OSP-AH-StxB1 and 98% for OSP-StxB1. At 1/10,000 dilution, the sera from mice injected with OSP-StxB1 had a significantly higher neutralization titer (70%) than the sera elicited by O-SP-AH StxB1 (34%). None of the sera from mice injected with either conjugate showed neutralization against Stx2. Both conjugates elicited levels of bactericidal antibodies against *E. coli* O157 that were roughly proportional to the content of IgG anti-LPS; this activity was removed by absorption with *E. coli* O157 LPS.

DISCUSSION

The O-SP of *E. coli* O157 LPS is a linear copolymer composed of the tetrasaccharide repeat unit: (→3)-α-D-GalpNAc-(1→2)-α-D-PerpNAc-(1→3)-α-L-Fucp-(1→4)-β-D-Glcp-(1→). It is non-immunogenic, probably due to its comparatively low molecular weight. As with other polysaccharides, its immunogenicity is increased by binding it to proteins to form a conjugate. Of the three conjugates of the present invention shown in Table 1, none elicited fever or significant local reactions in human volunteers, and all volunteers responded with a ≧4-fold rise in serum IgG anti-*E. coli* O157 LPS that was sustained 26 weeks after injection. (Re-injection of the *E. coli* O157 O-SP conjugates was not attempted because of the failure of other polysaccharide conjugates to induce a booster response in adults.)

These volunteers, like most adults, had low levels of "natural" serum anti *E. coli* O157 LPS probably induced by cross-reacting antigens [32, 33, 34, 35]. This is typical for other bacterial pathogens as well. Higher levels of anti-O157 LPS antibodies are found in patients with HUS, and in individuals involved in raising cattle in certain areas, probably as a result of previous contact with these organisms. Although the unusual monosaccharide perosamine is found in the O-SP of both *E. coli* O157 and *V. cholerae* O1, we have not been able to detect a cross-reaction between human antibodies to these two antigens. The conjugate prepared from the O-SP obtained by acetic acid hydrolysis (O-SP-rEPA) elicited significantly higher levels of anti-O157 LPS at four weeks than did conjugates prepared with hydrazine-treated LPS. The LPS and ETA antibody levels, however, at 26 weeks post-injection were similar in all three groups (Table 1). As reported for patients with shigellosis and for adults vaccinated with Shigella conjugates, serum IgG anti-LPS rose to the highest level and was the most sustained of the three serum immunoglobulins [13, 15, 34, 36, 37]. Similar results were obtained in mice for the IgG anti-LPS responses elicited by *E. coli* O111 conjugates [38].

The protective action of existing vaccines may be due to the induction of a critical level of specific IgG antibodies that, in many cases, inactivate the inoculum of the pathogen on epithelial surfaces including the intestine [39, 40]. It is not commonly appreciated that serum IgG is a major immunoglobulin component of secretory fluids including that of the small intestine. As has been observed in mice [8], all three conjugates induced IgG anti-LPS with bactericidal activity in the volunteers (Table 2). Serum IgG anti-polysaccharide is the major, if not the sole host component, that confers immunity induced by these conjugates. Accordingly, it should be possible to standardize the potency of *E. coli* O157 conjugates by chemical assay and by measurement of serum IgG anti-polysaccharide as has been done for *Haemophilus influenzae* type b conjugate vaccines.

The 1995 outbreak of *E. coli* O157 infection in Japan lasted several months, partly due to the failure to identify the bacterial sources [41]. Most of the volunteers (81%) responded with nearly a 10-fold increase in IgG anti-LPS 1 week after vaccination, indicating that the vaccine of this invention could serve to control *E. coli* O157 infection during an outbreak. Another use for the *E. coli* O157 conjugates of this invention would be to prepare high-titered IgG anti-LPS globulin for prophylaxis and treatment of case contacts during an outbreak. It has been suggested that antibiotic treatment of patients increases the incidence of HUS, possibly by causing lysis of the *E. coli* O157 with release of additional Shiga toxins. Clinical and experimental data point to LPS as the pathogenic agent for HUS and the other extraintestinal lesions following infection with enteric Gram-negative pathogens [42, 43]. There is also a suggestion of a direct role of Shiga toxins on renal tissue involvement in HUS [44]. The present invention provides a solution to this problem in the form of a conjugate of *E. coli* O157 O-SP with the B subunit of Shiga toxin 1. In mice, this conjugate induces both serum IgG anti-LPS and neutralizing antibodies to Shiga toxin 1.

The data show that the various *E. coli* O157 LPS-protein conjugates disclosed herein will generate high antibody levels in humans (i.e., approximately 5-10 times more IgG in humans than in mice) and high neutralization antibody titers in humans (i.e., $10^3$ to $10^4$ in humans as opposed to $10^2$ in mice). The data also show that the various *E. coli* O157 LPS-protein conjugates disclosed herein will generate a greater than 4-fold rise in IgG antibody levels in about 80% of human subjects one week after a single injection and in all human subjects 4 weeks after a single injection.

REFERENCES AND NOTES

1. For reviews, see:
    (a) J. B. Robbins, R. Schneerson, S. Szu, V. Pozsgay, In: *Vaccinia, vaccinations and vaccinology: Jenner, Pasteur and their successors* (Ed.: S. Plotkin, B. Fantini), Elsevier, Paris, p. 135-143 (1996).
    (b) R. K. Sood, A. Fattom, V. Pavliak, R. B. Naso, *Drug Discovery Today*, 1, 381-387 (1996).
    (c) H. J. Jennings, R. K. Sood, In *Neoglycoconjugates. Preparation and Applications* (Eds. Y. C. Lee, R. T. Lee), Academic Press, New York, pp. 325-371 (1994).
2. K. Landsteiner, *The specificity of serological reactions*, Harvard University Press, Cambridge, (1970).
3. R. Schneerson, O. Barrera, A. Sutton, J. B. Robbins, *J. Exp. Med.* 1980, 152, 361-376.
4. J. B. Robbins, R. Schneerson, P. Anderson, D. H. Smith, *J. Am Med. Assoc.* 1996, 276, 1181-1185.
5. For example:
    (a) Cohen, D., et al., *Lancet*, 349, 155-0159 (1997).
    (b) Cohen, D., et al., *Infect. Immun.*, 64, 4074-4077 (1997).
6. Riley. L. W., et al., *N. Engl. J. Med.*, 308, 681-685 (1983).
7. Takeda, Y., *World Health Statistics Quarterly*, 50, 74-80 (1997)
8. Konadu et al., *Infection & Immunity*, 62, 5048-5054 (1994)
9. Robbins, J. B., et al., *Clin. Infect. Dis.*, 15, 346-361 (1992)
10. Konadu et al., *Journal of Infectious Diseases*, 177 383-387 (1998)
11. Butler, T., Islam, M. R., Azad, M. A. K., Jones, P. K., *J. Pediatr.*, 110, 894-897 (1987)
12. Proulx, F., et al., *J. Pediatr.*, 121, 299-303 (1992).
13. Cohen, D, C. Block, M. S. Green, G. Lowell, and I. Ofek, *J. Clin. Microbiol.*, 27, 162-167 (1989).
14. Cohen, D., M. S. Green, C. Block, T. Roauch, and I. Ofek, *J. Infect. Dis.*, 157, 1068-1071 (1988).
15. Robbins, J. B., and R. Schneerson, *J. Infect. Dis.*, 161, 821-832 (1990).
16. Taylor, D. N., et al., *Infect. Immun.*, 61, 3678-3687 (1993).
17. Cohen, D., S. Ashkenazi, et al., *Lancet*, 349, 155-159 (1997).
18. Cryz, S. J., et al., *J. Infect. Dis.*, 163, 1040-1045 91991).
19. Weinstein, D. L., Jackson, M. P., Perera, L. P., Holmes, R. K., O'Brien, A. D., *Infect. Immun.*, 57, 3743-3750 (1989)
20. Acheson, et al., *Infect. Immun.*, 61, 1098-1104 (1993).
21. Pozsgay, V., Trinh, L., Shiloach, J., Robbins, J. B., Donohue-Rolfe A, Calderwood S B., *Bioconjugate. Chem.*, 7, 45-55 (1996).
22. Fattom, A., C. Lue, S. C. Szu, J. Mestecky, G. Schiffman, D. A. Bryla, W. F. Vann, D. Watson, L. M. Kimzey, J. B. Robbins, and R. Schneerson, *Infect. Immun.*, 58, 2309-2312 (1990).
23. Devi, S. J., J. B. Robbins and R. Schneerson., *Proc. Natl. Acad. Sci. USA* 88:7175-7179, 1991 (1992).
24. Szu, S. C., X. Li, A. L. Stone, and J. B. Robbins, *Infect. Immun.* 59 4555-4561 (1991).
25. Szu, S. C., A. L. Stone, J. D. Robbins, R. Schneerson, and J. B. Robbins, *J. Exp. Med.* 166 1510-1524 (1987).
26. C. Chu, et al., *Infect. Immun.*, 59, 4450-4458 (1991).
27. Kohn, J., Wilchek, M., *FEBS Letters*, 154, 209 (1983).
28. Aleksic, S., Karch, H., Bockemühl, J., *Int. J. Med. Microbiol.*, 276, 221-230 (1992).
29. Lees, A., Nelson, B., Mond, J. J., *Vaccine.*, 14, 190-198 (1995).
30. Konadu, E., Shiloach, J., Bryla, D. A., Robbins, J. B., Szu, S. C., *Infect. Immun.*, 64, 2709-2715 (1996).
31. Gentry M., Dalrymple J. M., *J. Clin. Micro.* 12, 361-366 (1980).
32. Chart, H, Rowe, B., *Lancet*, 341, 1282 (1993).
33. Robbins J. B., Schneerson R., *J Infect Dis.*, 161, 821-832 (1990).
34. Greatorex J. S., Thorni G. M., *J Clin Microbiol.*, 32, 1172-1178 (1994).
35. Cohen, D., et al., *Infect Immun.*, 64, 4074-4077 (1996).
36. Ekwall E, et al., *Serodiag. Immunother. Infect. Dis.*, 2, 171-182 (1988).
37. Cohen D., et al., *Infect Immun.*, 64, 4074-4077 (1996).
38. Gupta, R. K., Egan W, Bryla D A, Robbins J B, Szu S C., *Infect. Immun.*, 63, 2805-2810 (1995).
39. Farmer, J. J., et al., *J Clin Microbiol.*, 21, 46-76 (1985).
40. Chart, H., Scotland, S. M., Rowe, B., *J Clin Microbiol.*, 27, 285-290 (1989).
41. Watanabe, H., Wada, A., Inagak, Y., Tamura, K., *Lancet*, 348, 831-832 (1996).
42. Koster, .F, et al., *N. Engl. J. Med.*, 298, 927-933 (1978).
43. Jalkanen, K. S., et al., *Lancet*, i, 685-688 (1990).
44. Pickering, L. K., Obrig, T. G., Stapleton, F. B., *Pediatr. Infect. Di.s J.*, 13, 459-476 (1994).

All of the references referred to above are hereby incorporated by reference in their entirety.

The invention claimed is:

1. A method for inducing an immune response in a human against *E. coli* O157, comprising administering to the human, in a physiologically acceptable agent, a conjugate molecule comprising about 5 µg to about 50 µg of *E. coli* O157 O-specific polysaccharide covalently bound to *P. aeruginosa* recombinant exoprotein A (rEPA), thereby inducing an immune response.

2. The method of claim 1, comprising 25 µg of the *E. coli* O157 O-specific polysaccharide.

3. The method of claim 1, wherein the human is under six years of age.

4. The method of claim 3, wherein the human is two to five years of age.

5. The method of claim 1, wherein the immune response comprises induction of anti-*E. coli* O157 O-specific polysaccharide serum antibodies.

6. The method of claim 5, wherein the anti-*E. coli* O157 O-specific polysaccharide serum antibodies are IgG antibodies.

7. The method of claim 5, wherein the anti-*E. coli* O157 O-specific polysaccharide serum antibodies have bacteriostatic or bactericidal activity against *E. coli* O157.

8. The method of claim 1, wherein the immune response protects the human against infection by *E. coli* O157.

9. The method of claim 1, wherein the *E. coli* O157 O-specific polysaccharide is covalently bound to the *P. aeruginosa* recombinant exoprotein A (rEPA) by means of a dicarboxylic acid dihydrazide linker.

10. The method of claim 9, wherein the dicarboxylic acid dihydrazide is adipic acid dihydrazide.

* * * * *